United States Patent [19]
Allgeier et al.

[11] 3,946,032
[45] Mar. 23, 1976

[54] ACETAL DERIVATIVES OF 6-PHENYL-4H-S-TRIAZOLO[4,3-A][1,4]BENZODIAZEPINE-1-CARBOXALDEHYDE

[75] Inventors: Hans Allgeier, Haagen, Germany; Andre Gagneux, Basel, Switzerland

[73] Assignee: Ciba-Geigy Corporation, Ardsley, N.Y.

[22] Filed: Oct. 12, 1973

[21] Appl. No.: 406,060

Related U.S. Application Data

[62] Division of Ser. No. 239,780, March 30, 1972, Pat. No. 3,867,536.

[30] Foreign Application Priority Data

Apr. 8, 1971  Switzerland.......................... 5233/71

[52] U.S. Cl. 260/308 R; 260/239 BD; 260/239.3 D; 260/338; 260/340.7; 260/340.9; 260/535 R; 260/561 H; 424/269
[51] Int. Cl.²........................................ C07D 487/04
[58] Field of Search ................................ 260/308 R

[56] References Cited
UNITED STATES PATENTS
3,681,343  8/1972  Hester............................ 260/308 R

*Primary Examiner*—Alton D. Rollins
*Attorney, Agent, or Firm*—Joseph G. Kolodny; John J. Maitner; Theodore O. Groeger

[57] ABSTRACT

Compounds of the class of acetals of 6-phenyl-4H-s-triazolo[4,3-a][1,4]benzodiazepine-1-carboxaldehyde and the 5-oxides and pharmaceutically acceptable acid addition salts thereof have valuable pharmacological properties, in particular anticonvulsant effectiveness. Further, they show central depressant and muscle-relaxing activity and are active ingredients for therapeutic preparations. Specific embodiments are 6-phenyl-8-chloro-4H-s-triazolo[4,3-a][1,4]benzodiazepine-1-carboxaldehyde-diethylacetal, 6-(o-chlorophenyl)-8-chloro-4H-s-triazolo[4,3-a][1,4]benzodiazepine-1-carboxaldehyde-diethylacetal and 6-(o-fluorophenyl-8-chloro-4H-s-triazolo[4,3-a][1,4]benzodiazepine-1-carboxaldehyde-diethylacetal.

11 Claims, No Drawings

ACETAL DERIVATIVES OF 6-PHENYL-4H-S-TRIAZOLO[4,3-A][1,4]BENZODIAZEPINE-1-CARBOXALDEHYDE

CROSS-REFERENCE TO RELATED APPLICATION

This is a division of application Ser. No. 239,780, filed Mar. 30, 1972, now U.S. Pat. No. 3,867,536.

DETAILED DESCRIPTION

The present invention relates to new diazepine derivatives, to processes for their production, to pharmaceutical compositions containing the new compounds, and to the use thereof.

The new diazepine derivatives correspond to the general formula I:

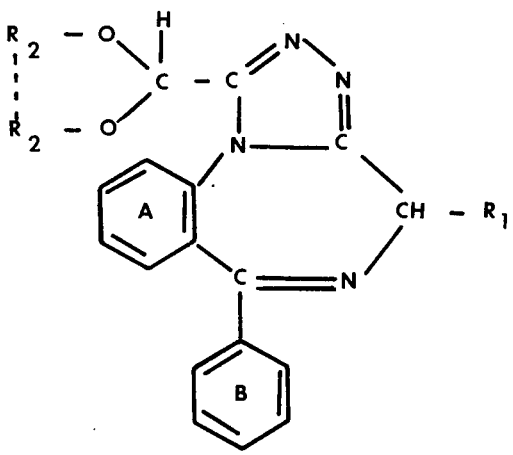

wherein
$R_1$ represents a hydrogen atom of an alkyl group having from 1 to 3 carbon atoms, and either
each of the symbols $R_2$ represents an alkyl group having from 1 to 4 carbon atoms, or
the symbols $R_2$ together represent a bivalent, saturated aliphatic hydrocarbon radical having from 2 to 5 carbon atoms,
and wherein each of the rings A and B, independently of the other, may be substituted by one or more bromine, chlorine and/or fluorine atoms and/or trifluoromethyl groups, nitro groups, alkyl groups containing from 1 to 6 carbon atoms and/or alkoxy groups containing from 1 to 6 carbon atoms.

The invention also relates to the 5-oxides of the compounds of the general formula I, and to the addition salts of the compounds of the general formula I with inorganic and organic acids.

As an alkyl group in the compounds of the general formula I, $R_1$ is, e.g. the methyl, ethyl or propyl group. $R_2$ as an alkyl group is, e.g. the propyl, isopropyl, butyl, isobutyl or sec.butyl group, and particularly the methyl or ethyl group; or —$R_2.R_2$— as a saturated aliphatic hydrocarbon radical having 2 to 5 carbon atoms is, e.g. the ethylene, propylene, ethyl-ethylene, trimethylene, tetramethylene, 2,2-dimethyl-trimethylene, or the 2-ethyl-trimethylene group.

Halogen atoms as substituents of the rings A and B are fluorine, chlorine or bromine atoms; whilst as alkyl groups or alkoxy groups having 1 to 6 carbon atoms, the following are, for example, suitable: methyl, ethyl, propyl, isopropyl, butyl, isobutyl, tert.butyl, pentyl, isopentyl, 2,2-dimethyl-propyl, hexyl or isohexyl groups, or methoxy, ethoxy, propoxy, isopropoxy, butoxy, isobutoxy, pentyloxy, isopentyloxy, 2,2-dimethyl-propoxy, hexyloxy or isohexyloxy groups. A substituent of ring A is, in particular, in the 8-position, and is preferably fluorine, bromine, the nitro group, the trifluoromethyl group and, in particular, chlorine. Ring B is preferably unsubstituted, or substituted by fluorine, chlorine or bromine in any desired position, especially, however, by fluorine or chlorine in the o-position.

The compounds of the general formula I, their 5-oxides and their addition salts with inorganic and organic acids possess valuable pharmacological properties. They exhibit, in particular, anticonvulsive and central-depressant activity and relax the muscular system. The anticonvulsive effectiveness can be determined, e.g. in the pentetrazole convulsion test on the mouse with oral doses from ca. 0.02 mg/kg, as well as in the strychnin convulsion test, in the electric shock test, and in the psychomotor electric shock test on the mouse after oral administration. The central-depressant activity is shown, for example, from the anaesthetic-potentiating effectiveness on the mouse after oral administration; this is, however, less pronounced compared with the anticonvulsive activity. The muscle-relaxing activity is reflected, for example, in the inhibition of polysynaptic reflexes on the rabbit after intravenous administration. The mentioned properties and others, which can be determined by selected standard tests [cp. W. Theobald and H. A. Kunz, Arzneimittelforsch. 13, 122 (1963), and W. Theobald et al., Arzneimittelforsch. 17, 561 (1967)], characterise the compounds of the general formula I, their 5-oxides, as well as their physiologically tolerable addition salts with inorganic and organic acids, as active substances for tranquillisers, sedatives, muscle-relaxants and anti-epileptics which are applicable, e.g. for the treatment of states of tension and agitation, for the lowering of the tension of the striated muscular system, as well as for the treatment of epilepsy.

Compounds of the general formula I which are of particular importance are those in which $R_1$ represents hydrogen or the methyl group, and $R_2$ the methyl or ethyl group, the ring A is unsubstituted or substituted by fluorine, chlorine, bromine, the nitro or trifluoromethyl group, and the ring B is either unsubstituted or carries at least one of the substituents metioned for ring A, especially fluorine, chlorine or bromine, with preferably at least one of the rings A and B being substituted. Particularly valuable compounds within this group are those having the general formula I a

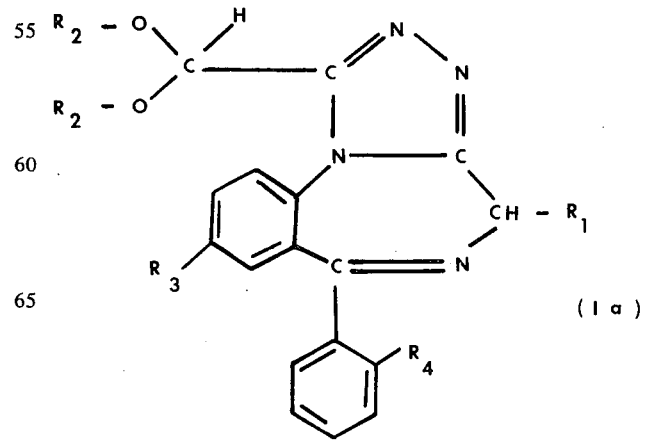

(I a)

wherein

R₁ represents a hydrogen atom or a methyl or ethyl group, each of the symbols R₂ represents a methyl or ethyl group, and R₃ and R₄, independently of each other represent hydrogen, a chlorine, fluorine or bromine atom, or a nitro or trifluoro methyl group, at least one of the symbols R₃ and R₄ being other than hydrogen Of the compounds of the general formula I a, those are most preferred wherein R₁ is hydrogen, R₂ is a methyl or ethyl group, R₃ is hydrogen or a chlorine atom and R₄ is hydrogen or a fluorine or chlorine atom, at least one of the symbols R₃ and R₄ being other than hydrogen.

Mentioned as examples of highly effective compounds from this group are: 6-phenyl-8-chloro-4H-s-triazolo[4,3-a][1,4]benzodiazepine-1-carboxaldehyde-diethylacetal, 6-(o-fluorophenyl)-8-chloro-4H-s-triazolo[4,3-a][1,4]benzodiazepine-1-carboxaldehyde-diethylacetal, 6-(o-chlorophenyl)-8-chloro-4H-s-triazolo[4,3-a][1,4]benzodiazepine-1-carboxaldehyde-diethylacetal, and 6-(o-chloro-phenyl)-4H-s-triazolo[4,3-a][1,4]benzodiazepine-1-carboxaldehyde-diethylacetal, 5-Oxides of the compounds of the general formula I, and particularly of the preferred types, in addition to having valuable pharmacological properties themselves, are of importance also as intermediates for the production of further pharmacologically effective compounds.

The new compounds of the general formula I, their 5-oxides and their addition salts are produced with application of a first process according to the invention by the condensation of a compound of the general formula II:

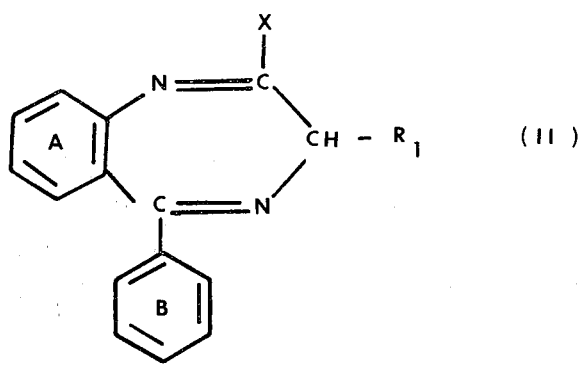

wherein

X represents a mercapto group, a lower alkoxy or alkylthio group optionally activated by a substituent, or an optionally mono- or disubstituted amino group, R₁ has the meaning given under formula I, and the rings A and B can be substituted as stated under formula I, with a compound of the general formula III:

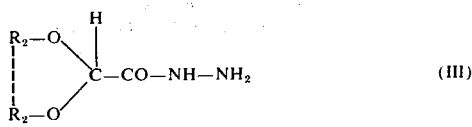

wherein R₂ or —R₂.R₂— has the meaning given under formula I; and, optionally, the oxidation of the obtained reaction product to its 5-oxide, or the conversion thereof into an addition salt with an inorganic or organic acid.

As lower alkylthio groups, X is preferably the methylthio or ethylthio group, and as alkoxy groups the methoxy or ethoxy group. These groups can be activated by a substituent. Such activated groups are, e.g. the o- or p-nitrobenzylthio group and the o- or p-nitrobenzyloxy group, respectively. As a mono-substituted amino group, X is, in particular, a lower alkylamino group such as the methylamino group, or an aralkylamino group such as the benzylamino group. As disubstituted amino group, X is, in particular, a lower dialkylamino group such as the dimethylamino group.

The reaction according to the invention is preferably performed at a reaction temperature of ca. 80° to 160°C in an inert solvent. Suitable inert solvents are, for example, hydrocarbons such as toluene or xylene, halogenated hydrocarbons such as chlorobenzene, a lower alkanol, preferably one agreeing with that of the acetal grouping, such as, e.g. ethanol or butanol, ethereal liquids such as diethylene glycol dimethyl ether, diethylene glycol diethyl ether, or dioxane and amides, especially N,N,N',N',N'',N''-hexamethyl-phosphoric acid triamide, or sulphoxides such as dimethylsulphoxide. The reaction times are between ca. 1 hour and 24 hours.

Starting substances embraced by the general formula II are described in the literature; see, amongst others, L. H. Sternbach and E. Reeder, J.Org.Chem. 26, 1111 (1961), S. C. Bell et al., J.Med.Chem. 5, 63 (1962), G. A. Archer and L. H. Sternbach, J.Org.Chem. 29, 231 (1964) and J. Farber et al., J.Med.Chem. 7, 235 (1964). Furthermore, compounds embraced by the general formula III have been described, such as, e.g. dimethoxyacetic acid hydrazide (cp. E. J. Browne and J. B. Polya, J.Chem.Soc. 1962, 5149). Further compounds of the general formulae II and III can be produced analogously to the procedure for the known compounds. For example, further starting materials of the general formula II having an optionally substituted amino group X can be obtained by reduction of the corresponding 4-oxides described in the literature.

Suitable oxidising agents for the subsequent conversion of compounds of the general formula I into their 5-oxides are preferably hydrogen peroxide or peroxy acids, at a temperature of ca. 0° to 70°C. Suitable peroxy acids are, e.g. peroxyacetic acid, or peroxybenzoic acids such as peroxybenzoic acid or, in particular, m-chloroperoxybenzoic acid. The oxidising agents are preferably used in a solvent, e.g. peroxyacetic acid in acetic acid, and peroxybenzoic acid in halogenated hydrocarbons such as methylene chloride or chloroform.

Compounds of the general formula I or their 5-oxides, as well as their addition salts with inorganic or organic acids, are produced with application of a second process according to the invention by the reaction of an aldehyde of the general formula IV:

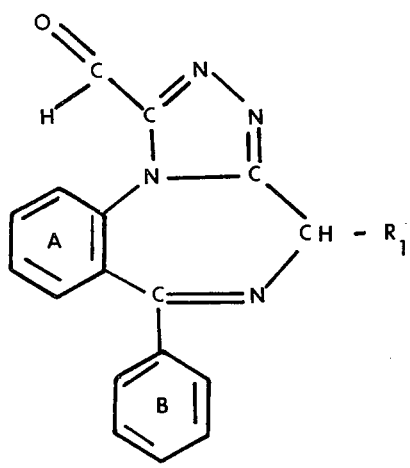

(IV)

wherein $R_1$ has the meaning given under formula I, and the rings A and B can be substituted as stated under formula I,
with a compound of the general formula V or VI:

$R_2$—OH (V)     $\begin{array}{l} R_2\text{—OH} \\ R_2\text{—OH} \end{array}$ (VI)

wherein $R_2$ or —$R_2.R_2$— has the meaning given under formula I; and, optionally the oxidation of the obtained reaction product to its 5-oxide, or the conversion of the said reaction product into an addition salt with an inorganic or organic acid.

The reaction according to the invention is preferably performed in a solvent, e.g. in an excess of the employed alkanol of the general formula V, or of an alkanediol of the general formula VI, in the presence of a catalyst. The catalyst used is, for example, a mineral acid, e.g. sulphuric acid or phosphoric acid, an aromatic sulphonic acid, e.g. the o- or p-toluenesulphonic acid, or a Lewis acid, e.g. boron trifluoride. The reaction is performed at a temperature of from ca. 20° to 170°C, particularly at the boiling temperature of the employed solvent.

The starting materials of the general formula IV can be obtained, for example, as follows: The starting compounds are compounds of the previously defined general formula II; these are reacted with benzyloxyacetic acid hydrazide to give corresponding 1-benzyloxymethyl-4H-s-triazolo[4,3-a][1,4]benzodiazepines, which are split with hydrobromic acid to corresponding 4H-s-triazolo[4,3-a][1,4]benzodiazepine-1-methanols; the obtained alcohols are subsequently oxidised with dimethylsulphoxide in the presence of dicyclohexylcarbodiimide and phosphoric acid.

The oxidation of the obtained compounds of the general formula I to their 5-oxides was described in conjunction with the first process.

The compounds of the general formula I, their 5-oxides, and their addition salts with inorganic or organic acids are obtained with application of a third process according to the invention by the condensation of a compound of the general formula VII:

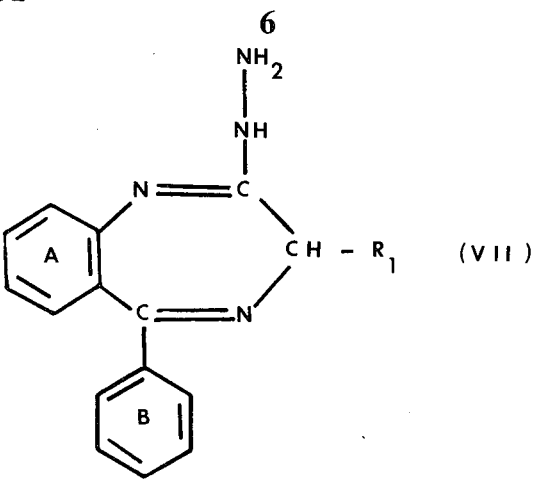

(VII)

wherein $R_1$ has the meaning given under formula I, and the rings A and B can be substituted as stated therein, with a reactive ester of a compound of the general formula VIII:

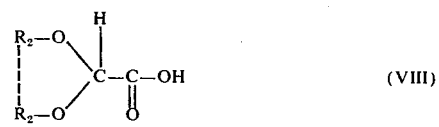

(VIII)

wherein $R_2$ or —$R_2.R_2$— has the meaning given under formula I; and, optionally, the oxidation of the obtained reaction product to its 5-oxide, or the conversion of the said reaction product into an addition salt with an inorganic or organic acid.

As reactive esters of a compound of the general formula VIII, it is possible to use, e.g. lower alkyl esters, particularly the methyl or ethyl ester.

The reaction according to the invention is preferably carried out at a reaction temperature of ca. 80° to 160°C in an inert solvent. Suitable inert solvents are, e.g. hydrocarbons such as toluene or xylene, halogenated hydrocarbons such as chlorobenzene, a lower alkanol, preferably one corresponding to the alkanol of the acetal grouping, such as, e.g. ethanol or butanol, ethereal liquids such as diethylene glycol methyl ether or dioxane, and amides, particularly N,N,N',N',N'',N''-hexamethyl-phosphoric acid triamide. The reaction times are between ca. 1 hour and 24 hours.

Starting materials of the general formula VII are known, e.g. 2-hydrazino-5-phenyl-7-chloro-3H-1,4-benzodiazepine (cp. Kanji Meguro and Yutaka Kuwada, Tetrahedron Letters 1970, 4039). Further compounds of this type can be produced analogously.

The oxidation of the obtained compounds of the general formula I to their 5-oxides was described in conjunction with the first process.

The compounds of the general formula I obtained by the processes according to the invention are optionally subsequently converted, in the usual manner, into their addition salts with inorganic and organic acids. For example, the acid desired as the salt component is added to a solution of a compound of the general formula I in an organic solvent. The organic solvents preferred for the reaction are ones in which the formed salt is difficultly soluble, and can hence be separated by filtration. Such solvents are, e.g. methanol, ether, acetone, methyl ethyl ketone, acetone/ether, acetone/ethanol, methanol/ether or ethanol/ether.

For use as pharmaceutical compositions it is possible to use, instead of free bases, physiologically tolerable acid addition salts, i.e. salts with such acids of which the anions are not toxic in the dosage amounts concerned. Moreover, it is of advantage if the salts to be used as pharmaceutical compositions crystallise well, and are not, or only slightly, hygroscopic. For salt formation with compounds of the general formula I it is possible to use, e.g. hydrochloric acid, hydrobromic acid, sulphuric acid, phosphoric acid, methanesulphonic acid, ethanesulphonic acid, 2-hydroxyethanesulphonic acid, or perchloric acid.

The new active substances are administered orally, rectally or parenterally. The dosage depends on the manner of administration, on the age, and on the individual condition.

The daily dosages of the free bases, their 5-oxides, and of physiologically tolerable acid addition salts of the free bases vary between 0.02 and 4 mg/kg for warm-blooded animals. Suitable dosage units, such as dragees, tablets or suppositories, preferably contain 0.5 – 25 mg of an active substance according to the invention.

Dosage units for oral administration contain as active substance preferably between 1 – 50% of a compound of the general formula I, of its 5-oxide or of a corresponding physiologically tolerable salt. They are produced by combining the active substance, e.g. with solid pulverulent carriers such as lactose, saccharose, sorbitol, mannitol; starches such as potato starch, maize starch or amylopectin, also laminaria powder or citrus pulp powder; cellulose derivatives or gelatine, optionally with the addition of lubricants such as magnesium or calcium stearate, or polyethylene glycols, to form tablets or dragee cores. The dragee cores are coated, e.g. with concentrated sugar solutions which may also contain, e.g. gum arabic, talcum and/or titanium dioxide; or with a lacquer dissolved in readily volatile organic solvents or mixtures of solvents. Dyestuffs can be added to these coatings, e.g. to distinguish between varying dosages of active substance.

Further dosage units suitable for oral administration are hard gelatine capsules, as well as soft closed capsules made from gelatine and a softener, such as glycerin. The hard capsules preferably contain the active substance as a granulate, e.g. in admixture with fillers such as maize starch, and/or lubricants such as talcum or magnesium stearate, and optionally stabilisers such as sodium metabisulphite ($Na_2S_2O_5$) or ascorbic acid. In soft capsules, the active substance is preferably dissolved or suspended in suitable liquids such as polyethylene glycols, whereby stabilisers may also be added.

Suitable dosage units for rectal administration are, e.g. suppositories consisting of a combination of an active substance with a suppository base material. Suitable suppository base materials are, e.g. natural or synthetic triglycerides, paraffin hydrocarbons, polyethylene glycols, or higher alkanols. Also suitable are gelatine rectal capsules consisting of a combination of the active substance with a base material. Suitable as a base material are, e.g. liquid triglycerides, polyethylene glycols, or paraffin hydrocarbons.

Ampoules for parenteral administration, especially intramuscular administration, preferably contain a water-soluble salt of an active substance in a concentration of preferably 0,1 – 1%, optionally together with suitable stabilisers and buffer substances, in aqueous solution.

The following prescriptions further illustrate the production of tablets, dragees, capsules, suppositories and ampoules:

a. 50 g of 6-phenyl-8-chloro-4H-s-triazolo[4,3-a][1,4]benzodiazepine-1-carboxaldehyde-diethylacetal are mixed with 175.8 g of lactose and 169.70 g of potato starch; the mixture is then moistened with an alcoholic solution of 10 g of stearic acid, and granulated through a sieve. After drying the granulate, 160 g of potato starch, 200 g of talcum, 2.50 g of magnesium stearate and 32 g of colloidal silicon dioxide are mixed in; the mixture is subsequently pressed into 10,000 tablets each weighing 80 mg and each containing 5 mg of active substance. The tablets can, if required, be provided with grooves for a more precise adjustment of the dosage amount.

b. A granulate is produced from 50 g of 6-phenyl-8-chloro-4H-s-triazolo[4.3-a][1,4]benzodiazepine-1-carboxaldehyde-diethylacetal, 175.90 g of lactose, and the alcoholic solution of 10 g of stearic acid. After drying of the granulate, it is mixed with 56.60 g of colloidal silicon dioxide, 165 g of talcum, 20 g of potato starch and 2.50 g of magnesium stearate; the mixture is then pressed into 10,000 dragee cores. These are subsequently coated with a concentrated syrup made from 502.28 g of crystallised saccharose, 6 g shellac, 10 g of gum arabic, 0.22 g of dyestuff and 1.5 g of titanium dioxide; they are then dried. The obtained dragees each weigh 100 mg and each contain 5 mg of active substance.

c. To produce 1000 capsules each containing 5 mg of active substance, 5 g of 6-phenyl-8-chloro-4H-s-triazolo[4,3a][1,4]benzodiazepine-1-carboxaldehyde-diethylacetal are mixed with 268.0 g of lactose; the mixture is evenly moistened with an aqueous solution of 2.0 g of gelatine, and then granulated through a suitable sieve (e.g. sieve III, Ph.Helv. V). The granulate is mixed with 10.0 g of dried maize starch and 15.0 g of talcum; the mixture is then evenly filled into 1000 hard gelatine capsules, size 1.

d. A suppository base mixture is prepared from 1.0 g 6-phenyl-8-chloro-4H-s-triazolo[4,3-a][1,4]benzodiazepine-1-carboxaldehyde-diethylacetal and 169.0 g of adeps solidus; the mixture is then filled into 100 suppositories each containing 10 mg of active substance.

As active substances for the above described or other dosage units, e.g. the identical amounts of 6-(o-fluorophenyl)-8-chloro-4H-s-triazolo[4,3-a][1,4]benzodiazepine-1-carboxaldehyde-diethylacetal, 6-(o-chlorophenyl)-8-chloro-4H-s-triazolo[4,3-a][1,4]benzodiazepine-1-carboxaldehyde-diethylacetal, 6-(o-chlorophenyl)-4H-s-triazolo[4,3-a][1,4]benzodiazepine-1-carboxaldehyde-diethylacetal or 6-phenyl-8-chloro-4H-s-triazolo[4,3-a][1,4]benzodiazepine-1-carboxaldehyde-dimethylacetal can be used as well.

The following examples further illustrate the production of the new compounds of the general formula I, as well as of starting materials not hitherto known; these examples, however, in no way limit the scope of the invention. Temperatures are given in degrees Centigrade. For elution chromatography, silica gel Merck (registered Trademark), 0.05 to 0.2 mm grain, is used. The petroleum ether employed is always one having a boiling range of 40° to 65° C.

EXAMPLE 1

A solution of 60.0 g of 2-methylthio-5-phenyl-7-chloro-3H-1,4-benzodiazepine [cp. G. A. Archer et al., J.Org.Chem. 29, 231 (1964)] and 38.8 g of diethoxyacetic acid hydrazide in 460 ml of abs. hexamethylphosphoric acid triamide is heated for 6 hours at 140°. The solvent is then distilled off in vacuo, and the residue distributed between methylene chloride and water. The organic phase is separated, washed with saturated sodium chloride solution, dried over sodium sulphate, and concentrated by evaporation. The residue is recrystallised from ethyl acetate/ether/petroleum ether, whereupon pure 6-phenyl-8-chloro-4H-s-triazolo[4,3-a][1,4]benzodiazepine-1-carboxaldehyde-diethylacetal is obtained, which melts at 133°–135°.

The diethoxyacetic acid hydrazide used as starting material is prepared as follows:

a. An amount of 81.0 g of diethoxyacetic acid methyl ester is dissolved in 800 ml of abs. ethanol; an addition is made to the solution of 50.0 g of hydrazine hydrate, and the mixture allowed to stand for 20 hours at 25°. The reaction mixture is then filtered, the filtrate concentrated in vacuo, and the residue distilled. The obtained diethoxyacetic acid hydrazide boils at 120°–150°/0.005 Torr, M.P. 30°–40°.

EXAMPLE 2

A solution of 15.9 g of 2-(methylthio)-5-(o-fluorophenyl)-7-chloro-3H-1,4-benzodiazepine and 9.7 g of diethoxyacetic acid hydrazide in 100 ml of hexamethylphosphoric acid triamide is heated for 10 hours at 140°; processing is then carried out analogously to the procedure described in Example 1, and the residue recrystallised from ethyl acetate/petroleum ether to obtain 6-(o-fluorophenyl)-8-chloro-4H-s-triazolo[4,3-a][1,4]benzodiazepine-1-carboxaldehyde-diethylacetal, M.P. 120°–121°.

The following are obtained in an analogous manner: with the use of 16.7 g of 2-(methylthio)-5-(o-chlorophenyl)-7-chloro-3H-benzodiazepine:- 6-(o-chlorophenyl)-8-chloro-4H-s-triazolo[4,3-a][1,4]benzodiazepine-1-carboxaldehyde-diethylacetal, M.P. 120°–121.5° (from ethyl acetate/petroleum ether);

with the use of 14.0 g of 2-(methylthio)-5-phenyl-7-methyl-3H-1,4-benzodiazepine:- 6-phenyl-8-methyl-4H-s-triazolo-[4,3-a][1,4]benzodiazepine-1-carboxaldehyde-diethylacetal;

with the use of 17.3 g of 2-(methylthio)-5-phenyl-7-bromo-3H-1,4-benzodiazepine:- 6-phenyl-8-bromo-4H-s-triazolo[4,3-a][1,4]benzodiazepine-1-carboxaldehyde-diethylacetal; and with the use of 16.5 g of 2-(methylthio)-5-(o-methoxyphenyl)-7-chloro-3H-1,4-benzodiazepine:- 6-(o-methoxyphenyl)-8-chloro-4H-s-triazolo[4,3-a][1,4]benzodiazepine-1-carboxaldehyde-diethylacetal.

The substituted 2-(methylthio)-5-phenyl-3H-1,4-benzodiazepines required as starting materials for the aforementioned final materials are obtainable from the corresponding substituted 1,3-dihydro-5-phenyl-2H-1,4-benzodiazepine-2-thiones described in J.Org.-Chem. 29, 231 (1964) analogously to the process described therein for 2-(methylthio)-5-phenyl-7-chloro-3H-1,4-benzodiazepine.

The following are moreover likewise obtained analogously to the above example:

from 15.7 g of 2-(methylthio)-3-methyl-5-phenyl-7-chloro-3H-1,4-benzodiazepine:- 3-methyl-6-phenyl-8-chloro-4H-s-triazolo[4,3-a][1,4]benzodiazepine-1-carboxaldehyde-diethylacetal, M.P. 151°–153° (from ethyl acetate/petroleum ether);

from 14.2 g of 2-(methylthio)-5-phenyl-7-fluoro-3H-1,4-benzodiazepine:- 6-phenyl-8-fluoro-4H-s-triazolo[4,3-a][1,4]benzodiazepine-1-carboxaldehyde-diethylacetal;

from 15.7 g of 2-(methylthio)-5-(o-tolyl)-7-chloro-3H-1,4-benzodiazepine:- 6-(o-tolyl)-8-chloro-4H-s-triazolo[4,3-a][1,4]benzodiazepine-1-carboxaldehyde-diethylacetal; from 14.8 g of 2-(methylthio)-5-phenyl-7-methoxy-3H-1,4-benzodiazepine:- 6-phenyl-8-methoxy-4H-s-triazolo[4,3-a][1,4]benzodiazepine-1-carboxaldehyde-diethylacetal;

from 16.7 g of 2-(methylthio)-5-phenyl-7-(trifluoromethyl)-3H-1,4-benzodiazepine:- 6-phenyl-8-(trifluoromethyl)-4H-s-triazolo[4,3-a][1,4]benzodiazepine-1-carboxaldehyde-diethylacetal;

from 16.7 g of 2-(methylthio)-5-($\alpha,\alpha,\alpha$-trifluoro-o-tolyl)-3H-1,4-benzodiazepine:- 6-($\alpha,\alpha,\alpha$-trifluoro-o-tolyl)-4H-s-triazolo[4,3-a][1,4]benzodiazepine-1-carboxaldehyde-diethylacetal;

from 20.1 g of 2-(methylthio)-5-($\alpha,\alpha,\alpha$-trifluoro-o-tolyl)-7-(trifluoromethyl)-3H-1,4-benzodiazepine:- 6-($\alpha,\alpha,\alpha$-trifluoro-o-tolyl)-8-(trifluoromethyl)-4H-s-triazolo[4,3-a][1,4]benzodiazepine-1-carboxaldehyde-diethylacetal, and from 18.4 g of 2(methylthio)-5-($\alpha,\alpha,\alpha$-trifluoro-o-tolyl)-7-chloro-3H-1,4-benzodiazepine:- 6-($\alpha,\alpha,\alpha$-trifluoro-o-tolyl)-8-chloro-4H-s-triazolo[4,3-a][1,4]benzodiazepine-1-carboxaldehyde-diethylacetal.

The substituted 2-(methylthio)-5-phenyl-3H-1,4-benzodiazepines required as starting materials are obtained, starting with the correspondingly substituted 1,3-dihydro-5-phenyl-2H-1,4-benzodiazepin-2-ones, of which the compounds containing a trifluoromethyl group are described in the American Patent 3,341,392, and, in some cases, also in Helv.Chim. Acta 45, 2226 (1962), and the remaining four compounds in J.Org.-Chem. 27, 3788 (1962), by conversion into the corresponding 2-thiones, and reaction of these with dimethylsulphate in methanolic sodium hydroxide solution, analogously to the process described in J.Org.Chem. 29, 231 (1964).

EXAMPLE 3

A solution of 12.0 g of 2-methylthio-5-phenyl-7-chloro-3H-1,4-benzodiazepine and 7.0 g of dimethoxyacetic acid hydrazide (cp. E. J. Browne and J. B. Polya, J.Chem.Soc. 1962, 5149–5152) in 100 ml of abs. hexamethylphosphoric acid triamide is heated for 9 hours at 140°. The obtained 6-phenyl-8-chloro-4H-s-triazolo[4,3-a][1,4]benzodiazepine-1-carboxaldehyde-dimethylacetal melts at 166°–172°.

EXAMPLE 4

By reaction of 15.0 g of 2-(methylthio)-5-(o-chlorophenyl)-3H-1,4-benzodiazepine with 9.7 g of diethoxyacetic acid hydrazide in 100 ml of hexamethylphosphoric acid triamide, analogously to Example 1, and crystallisation of the crude product from ethyl acetate/petroleum ether, 6-(o-chlorophenyl)-4H-s-triazolo[4,3-a][1,4]benzodiazepine-1-carboxaldehyde-diethylacetal, M.P. 145°–146°, is obtained.

The 2-methylthio compound required as starting material is produced from the 1,3-dihydro-5-(o-chlorophenyl)-2H-1,4-benzodiazepin-2-one described by L. H. Sternbach et al., J.Med.Chem. 6, 261–265 (1963)

by conversion into the corresponding 2-thione, and reaction of this with dimethylsulphate in methanolic sodium hydroxide solution, analogously to the process described in J.Org.Chem. 29, 231 (1964), M.P. 109°–111° (from ethyl acetate/petroleum ether).

EXAMPLE 5

A solution of 7.0 g of 7-chloro-2-mercapto-5-phenyl-3H-1,4-benzodiazepine [cp. G. A. Archer and L. H. Sternbach, J.Org.Chem. 29, 231 (1964)] and 5.7 g of diethoxyacetic acid hydrazide in 50 ml of abs. ethanol is refluxed for 25 hours. The reaction mixture is concentrated in vacuo, and the obtained crude product is processed as described in Example 1, whereupon 6-phenyl-8-chloro-4H-s-triazolo[4,3-a][1,4]benzodiazepine-1-carboxaldehyde-diethylacetal, M.P. 133°–135°, is obtained.

EXAMPLE 6 a. A solution of 200 mg of 2-(dimethylamino)-5-phenyl-7-chloro-3H-1,4-benzodiazepine [cp. J. Farber et al., J.Med. Chem. 7, 235 (1964)] and 150 mg of diethoxyacetic acid hydrazide in 3 ml of abs. hexamethylphosphoric acid triamide is heated for 10 hours at 140°. The reaction mixture is concentrated in vacuo, and the crude product processed as described under Example 1, whereupon 6-phenyl-8-chloro-4H-s-triazolo[4,3-a][1,4]benzodiazepine-1-carboxaldehyde-diethylacetal, M.P. 133°–135°, is obtained.

b. The identical final material is obtained also by the use of the following starting materials, instead of 2-(dimethylamino)-5-phenyl-7-chloro-3H-1,4-benzodiazepine:

180 mg of 2-amino-5-phenyl-7-chloro-3H-1,4-benzodiazepine [cp. S. C. Bell et al., J.Med.Chem. 5, 63 (1962)], or 240 mg of 2-(benzylamino)-5-phenyl-7-chloro-3H-1,4-benzodiazepine (obtainable according to the British Patent 1,023,793, or from the 4-oxide described by S. C. Bell et al., loc.cit. analogously to L. H. Sternbach et al., loc.cit.), or 190 mg of 2-(methylamino)-5-phenyl-7-chloro-3H-1,4-benzodiazepine [cp. L. H. Sternbach et al., J.Org.-Chem. 26, 1111 (1961)].

The following are likewise obtained in an analogous manner:

with the use of 205 mg of 2-amino-5-phenyl-7-(trifluoromethyl)-3H-1,4-benzodiazepine:- 6-phenyl-8-(trifluoromethyl)-4H-s-triazolo[4,3-a][1,4]benzodiazepine-1-carboxaldehyde-diethylacetal;

with the use of 180 mg of 2-amino-5-phenyl-7-methoxy-3H-1,4-benzodiazepine:- 6-phenyl-8-methoxy-4H-s-triazolo[4,3-a][1,4]benzodiazepine-1-carboxaldehyde-diethylacetal, and with the use of 170 mg of 2-amino-5-phenyl-7-methyl-1H-1,4-benzodiazepine:- 6-phenyl-8-methyl-4H-s-triazolo[4,3-a][1,4]benzodiazepine-1-carboxaldehyde-diethylacetal.

The three aforementioned starting materials can be produced, for example, by the process of the German Offenlegungsschrift 1,933,986, Chemical Abstracts 72, 100772 h (1970), or analogously to the previously mentioned 2-amino compound.

EXAMPLE 7

A mixture of 300 mg of 6-phenyl-8-chloro-4H-s-triazolo[4,3-a][1,4]benzodiazepine-1-methanol, 0.57 g of dicyclohexyl-carbodiimide, 45 mg of phosphoric acid and 3 ml of abs. dimethylsulphoxide is stirred for 6 days at 25° and for a further 2 days at 70°–80°. Methylene chloride is then added, the organic phase washed with water and saturated sodium chloride solution, dried over magnesium sulphate and concentrated by evarporation. Crude 6-phenyl-8-chloro-4H-s-triazolo[4,3-a][1,4]benzodiazepine-1-carboxaldehyde is obtained, which is dissolved in 5 ml of ethanol. An addition is made to the obtained solution of 100 mg of p-toluenesulphonic acid, and the mixture refluxed for 10 hours. The solution is concentrated in vacuo. The residue is taken up in methylene chloride, the organic phase washed with 5% aqueous potassium carbonate solution and with saturated sodium chloride solution, dried over sodium sulphate, and concentrated by evaporation. The residue is recrystallised from ethyl acetate/ether/petroleum ether to obtain 6-phenyl-8-chloro-4H-s-triazolo[4,3-a][1,4]benzodiazepine-1-carboxaldehyde-diethylacetal, M.P. 133°–135°.

The starting compound is produced as follows:

a. A solution of 30 g of 2-methylthio-5-phenyl-7-chloro-3H-1,4-benzodiazepine [cp. G. A. Archer et al., J.Org.Chem. 29, 231 (1964)] and 19.8 g of benzyloxyacethydrazide [cp. Th. Curtius and N. Schwan, J.prakt. Chem. [2] 51, 353 (1895)] in 160 ml of hexamethylphosphoric acid triamide is heated for 8 hours at 140°. The solvent is then distilled off in vacuo, and the residue distributed between methylene chloride and water. The organic phase is separated, washed with saturated aqueous sodium chloride solution, dried over sodium sulphate and concentrated by evaporation. 1-benzyloxymethyl-6-phenyl-8-chloro-4H-s-triazolo[4,3-a][1,4]benzodiazepine crystallises out; it melts at 163°–165°.

b. An amount of 25 g of the compound prepared according to (a) is dissolved in 200 ml of glacial acetic acid; an addition of 170 ml of 48% hydrobromic acid is then made to the above solution. The mixture is refluxed for 90 minutes, cooled to 5° and, whilst stirring is maintained, adjusted with sodium hydroxide solution to pH 6; water and methylene chloride are then added. The organic phase is separated, washed with saturated aqueous sodium chloride solution, dried over sodium sulphate, and concentrated by evaporation. The residue is dissolved in ethyl acetate/methanol (9:1), the solution filtered through a column of 150 g of silicagel Merck (registered trademark), 0.05–0.2 mm grain, and the column eluted with ethyl acetate-methanol (9:1) to (7:3). The eluate is concentrated by evaporation and the residue crystallised from ethyl acetate/ether to obtain 6-phenyl-8-chloro-4H-s-triazolo[4,3-a][1,4]benzodiazepine-1-methanol, M.P. 209°–211°.

EXAMPLE 8

A solution of 2-hydrazino-5-phenyl-7-chloro-3H-1,4-benzodiazepine [cp. Kanji Meguro and Yutaka Kuwada, Tetrahedron Letters 1970, 4039 (1970)] and 5 g of diethoxyacetic acid ethyl ester in 50 ml of N,N,N',N',N'',N''-hexamethylphosphoric acid triamide is heated for 5 hours at 100°. The reaction mixture is then concentrated in vacuo, and the residue distributed between methylene chloride and water. The organic phase is washed with water and saturated sodium chloride solution, dried over sodium sulphate, and concentrated by evaporation. The residue is recrystallised from ethyl acetate/ether/petroleum ether, whereupon the obtained pure 6-phenyl-8-chloro-4H-s-triazolo[4,3-a][1,4] benzodiazepine-1-carboxaldehyde-diethylacetal melts at 133° – 135°.

EXAMPLE 9

A solution of 7.64 g (0.024 mole) of m-chloro-peroxybenzoic acid in 140 ml of methylene chloride is added dropwise within 15 minutes at 0°–5°, with stirring, to a solution of 9.0 g (0.0126 mole) of 6-phenyl-8-chloro-4H-s-triazolo[4,3-a][1,4]benzodiazepine-1-carboxaldehyde-diethylacetal in 100 ml of methylene chloride. The reaction mixture is stirred in a melting ice bath for a further 16 hours; the mixture is subsequently concentrated in vacuo and ether added to the residue. The precipitated crystals are filtered under suction, and washed twice with hot ethyl acetate. The obtained 6-phenyl-8-chloro-4H-s-triazolo[4,3-a][1,4]benzodiazepine-1-carboxaldehyde-diethylacetal-5-oxide melts at 200°–202°.

EXAMPLE 10

An amount of 0.13 g (0.0013 mole) of perchloric acid is added to a solution of 0.5 g (0.00126 mole) of 6-phenyl-8-chloro-4H-s-triazolo[4,3 -a][1,4]benzodiazepine-1-carboxaldehyde-diethylacetal in 3 ml each of acetone and methanol. The salt crystallises out after the addition of 5 ml of petroleum ether. Filtration under suction is then performed and 6-phenyl-8-chloro-4H-s-triazolo[4,3-a][1,4]benzodiazepine-1-carboxaldehyde-diethylacetal-perchlorate obtained, which decomposes at 250°–265°.

What we claim is:

1. A compound having the formula I a,

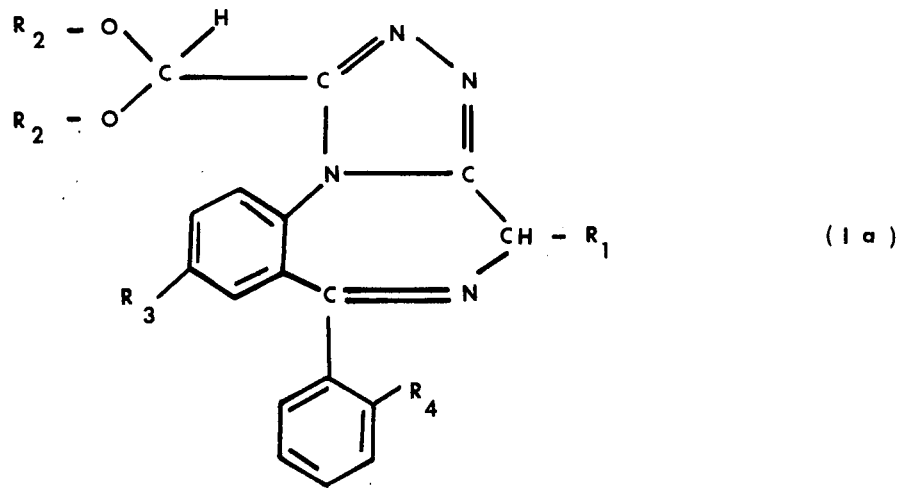

(I a)

wherein
$R_1$ represents a hydrogen atom or a methyl or ethyl group,
each of the symbols $R_2$ represents a methyl or ethyl group, and
$R_3$ and $R_4$, independently of each other, represents hydrogen, a chlorine, fluorine or bromine atom, or a nitro or trifluoromethyl group, at least one of the symbols $R_3$ and $R_4$ being other than hydrogen, as well as the 5-oxide thereof.

2. A compound according to claim 1 wherein $R_1$ represents hydrogen and each of the symbols $R_2$ and the symbols $R_3$ and $R_4$ have the meaning given in claim 1, and its 5-oxide.

3. A compound according to claim 1 wherein $R_1$ represents hydrogen, each of the symbols $R_2$ has the meaning given in claim 1, $R_3$ represents hydrogen or a chlorine atom and $R_4$ represents hydrogen or a chlorine or fluorine atom, at least one of the symbols $R_3$ and $R_4$ being other than hydrogen, and its 5-oxide.

4. A compound according to claim 1 wherein $R_1$ represents hydrogen, each of the symbols $R_2$ has the meaning given in claim 1, $R_3$ represents hydrogen or a chlorine atom and $R_4$ represents hydrogen or a chlorine or fluorine atom, at least one of the symbols $R_3$ and $R_4$ being other than hydrogen.

5. A compound according to claim 1 which is 6-phenyl-8-chloro-4H-s-triazolo[4,3-a][1,4]benzodiazepine-1-carboxaldehyde-dimethylacetal.

6. A compound according to claim 1 which is 6-phenyl-8-chloro-4H-s-triazolo[4,3-a][1,4]benzodiazepine-1-carboxaldehyde-diethylacetal.

7. A compound according to claim 1 which is 4-methyl-6-phenyl-8-chloro-4H-s-triazolo[4,3-a][1,4]benzodiazepine-1-carboxaldehyde-diethylacetal.

8. A compound according to claim 1 which is 6-(o-fluorophenyl)-8-chloro-4H-s-triazolo[4,3-a][1,4]benzodiazepine-1-carboxaldehyde-diethylacetal.

9. A compound according to claim 1 which is 6-(ochlorophenyl)-8-chloro-4H-s-triazolo[4,3-a][1,4]benzodiazepine-1-carboxaldehyde-diethylacetal.

10. A compound according to claim 1 which is 6-(o-chlorophenyl)-4H-s-triazolo[4,3][1,4]benzodiazepine-1-carboxaldehyde-diethylacetal.

11. A compound according to claim 1 which is 6-phenyl-8-chloro-4H-s-triazolo[4,3-a][1,4]benzodiazepine-1-carboxaldehyde-diethylacetal-5-oxide.

* * * * *